United States Patent
Gu (10) Patent No.: US 9,320,449 B2
(45) Date of Patent: Apr. 26, 2016

(54) METHOD AND SYSTEM FOR ON-LINE DECISION MAKING SUPPORT

(71) Applicant: Haisong Gu, Cupertino, CA (US)

(72) Inventor: Haisong Gu, Cupertino, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 716 days.

(21) Appl. No.: 13/623,320

(22) Filed: Sep. 20, 2012

(65) Prior Publication Data

US 2014/0081115 A1    Mar. 20, 2014

(51) Int. Cl.
*A61B 5/04*      (2006.01)
*A61B 5/0476*    (2006.01)
*A61B 5/00*      (2006.01)
*A61B 5/0478*    (2006.01)

(52) U.S. Cl.
CPC ............. *A61B 5/0476* (2013.01); *A61B 5/0478* (2013.01); *A61B 5/7246* (2013.01); *A61B 5/7267* (2013.01)

(58) Field of Classification Search
None
See application file for complete search history.

(56) References Cited

U.S. PATENT DOCUMENTS

| | | | | |
|---|---|---|---|---|
| 6,092,058 A | * | 7/2000 | Smyth | 706/10 |
| 7,403,814 B2 | | 7/2008 | Cox et al. | |
| 2006/0167371 A1 | * | 7/2006 | Flaherty et al. | 600/545 |
| 2010/0001036 A1 | | 1/2010 | Marczyk et al. | |
| 2010/0324440 A1 | * | 12/2010 | Moore et al. | 600/544 |
| 2011/0159467 A1 | * | 6/2011 | Peot et al. | 434/157 |

OTHER PUBLICATIONS

U. Herwig et al. "Using the International 10-20 EEG System for Positioning of Transcranial Magnetic Stimulation", Brian Topography, vol. 16, No. 2, 2003, pp. 95-99.

* cited by examiner

*Primary Examiner* — Etsub Berhanu
(74) *Attorney, Agent, or Firm* — Buchanan Ingersoll & Rooney PC (57) ABSTRACT

A method for on-line decision making support, which includes sensing biological signals of a subject upon detection of a decision making process during a performance of a task, and recording biological activity of the subject. Upon completing the decision making process, the recorded biological activity is released to a data processing system for analysis, which compares the recorded biological activity with a profile model for the subject and calculates a confident value for the recorded biological activity against the profile model for the subject. If the confident value does not meet a predefined threshold, a post-processing procedure is performed, wherein the predefined threshold represents a desired performance of the subject on the task.

19 Claims, 5 Drawing Sheets

METHOD AND SYSTEM FOR ON-LINE DECISION MAKING SUPPORT

FIELD

This invention relates to a method and system for on-line decision making support, and more particularly, a method and system for on-line decision making support, which senses biological signals, for example, brainwave activity, of a subject during a performance of a task, and calculates a confident value based on the biological signals or brainwave activity to determine if a post-processing procedure is necessary.

BACKGROUND

Many jobs involve the visual inspection either via image screening or human vision to identify operation threats or suspected issues. For example, a radiologist employs the use of imaging to both diagnose and treat diseases visualized within the human body. Radiologists use an array of imaging technologies (such as X-ray radiography, ultrasound, computed tomography (CT), nuclear medicine, positron emission tomography (PET) and magnetic resonance imaging (MRI) to observe and diagnose or treat diseases. Meanwhile, a surgeon employs a steerable medical device, which can be inserted into the body of the patient via an endoscope, which provides the surgeon with the ability to observe the procedure that is being performed within the patient.

In addition, video surveillance system operators and visual inspectors view one or more screens to identify operation threats or suspected issues for facility protection or assembly lines and the like. During the performance of the task, the operators or inspectors screen pictures or objects, which appear rapidly in order to identify operational threats or suspected issues. Thus, their performances and inspection results can heavily depend on personal knowledge, experiences and mental status.

In addition to visual inspections, acoustic inspections of musical instruments, gustatory or taste tests of food and drink, smell tests for foods and the like, and inspections using touch are often performed by subjects as part of an occupation or job, educational experience or daily activities.

So far there are few methods to measure the performance of these screening professionals, students and the like, directly based on biological activities. Accordingly, it would be desirable to have a scientific and objective way to measure the confidence of each inspection and/or activity, which would improve productivity related to visual, acoustic, gustatory or taste, smell, and/or touch inspections based on an objective mental measurement.

SUMMARY

In consideration of the above issues, it would be desirable to have a method and system, which provides for on-line (or real-time) decision making support by sensing biological activity, for example, brainwave activity, of a subject during a performance of a task and calculates a confident value based on the biological activity or brainwave activity to determine if a post-processing procedure is necessary.

In accordance with an embodiment, a method for on-line decision making support as disclosed, comprises: sensing biological signals of a subject upon detection of a decision making process during a performance of a task; recording biological activity of the subject; completing the decision making process and releasing the recorded biological activity to a data processing system for analysis; comparing the recorded biological activity with a profile model for the subject; calculating a confident value for the recorded biological activity against the profile model for the subject, and performing a post-processing procedure if the confident value does not meet a predefined threshold, wherein the predefined threshold represents a desired performance of the subject on the task.

In accordance with another embodiment, a system for on-line decision making as disclosed, comprises: a biological sensing device; and a computer device having executable instructions for generating a confident value for biological from the biological sensing device, comprising: sensing biological signals of a subject upon detection of a decision making process during a performance of a task; recording biological activity; completing the decision making process and releasing the biological activity to a data processing system for analysis; comparing the recorded biological activity with a profile model for the subject; calculating the confident value for the recorded biological activity against the profile model for the subject, and performing a post-processing procedure if the confident value does not meet a predefined threshold, wherein the predefined threshold represents a desired performance of the subject on the task.

In accordance with a further embodiment, a non-transitory computer readable medium containing a computer program for on-line decision making support as disclosed, comprises: sensing biological signals of a subject upon detection of a decision making process during a performance of a task; recording biological activity of the subject; completing the decision making process and releasing the recorded biological activity to a data processing system for analysis; comparing the recorded biological activity with a profile model for the subject; calculating a confident value for the recorded biological activity against the profile model for the subject, and performing a post-processing procedure if the confident value does not meet a predefined threshold, wherein the predefined threshold represents a desired performance of the subject on the task.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

Reference will now be made in detail to the embodiments of the invention, examples of which are illustrated in the accompanying drawings. Wherever possible, the same reference numbers are used in the drawings and the description to refer to the same or like parts.

A method for on-line decision making support as disclosed, includes sensing biological signals of a subject upon detection of a decision making process during a performance of a task; recording biological activity of the subject; completing the decision making process and releasing the recorded biological activity to a data processing system for analysis; comparing the recorded biological activity with a profile model for the subject; calculating a confident value for the recorded biological activity against the profile model for the subject, and performing a post-processing procedure if the confident value does not meet a predefined threshold, wherein the predefined threshold represents a desired performance of the subject on the task. As used herein biological activity relates to the study of life and living organisms, which can include biological activities such as perspiration or sweat, heart rate, nervous signals, brain waves, and/or combinations thereof. The biological activities can be measured with any suitable sensing devices, which can detect changes in biological activity of a subject. For example, brainwaves can be measured and/or detected using an EEG, wherein the EEG includes one or more electrodes, which detect visual stimuli or signals.

In accordance with an exemplary embodiment, the biological activity can include any activity related to an activity, which requires the subject to perform a visual, an acoustic, a gustatory or taste, a smell, and/or a touch activity and measuring responses associated therewith based on an objective measurement. In accordance with an embodiment, the biological sensor is a device which changes various types of physicochemical properties of target to a different state, for example electrical signals. For example, a heart rate monitor could be used for measuring the heart rate of a subject, or a temperature sensor for sensing changes in body temperature.

For example, neurophysiological research findings have shown that a stereotypical spatiotemporal electroencephalography (EEG) response can be triggered when a target image is shown among a sequence of non-target and/or distractor images. Accordingly, it would be desirable, to use these indices to monitor performance of visual inspectors, surgeons, video surveillance system operators and the like. In addition, the method and systems as disclosed herein can be used for acoustic inspections, for example, tuning of musical instruments, quality checking of cans, and the like, gustatory inspections, for example, taste tests of wine and other drinks and food, smell inspections, and inspections using touch.

Figure 1:
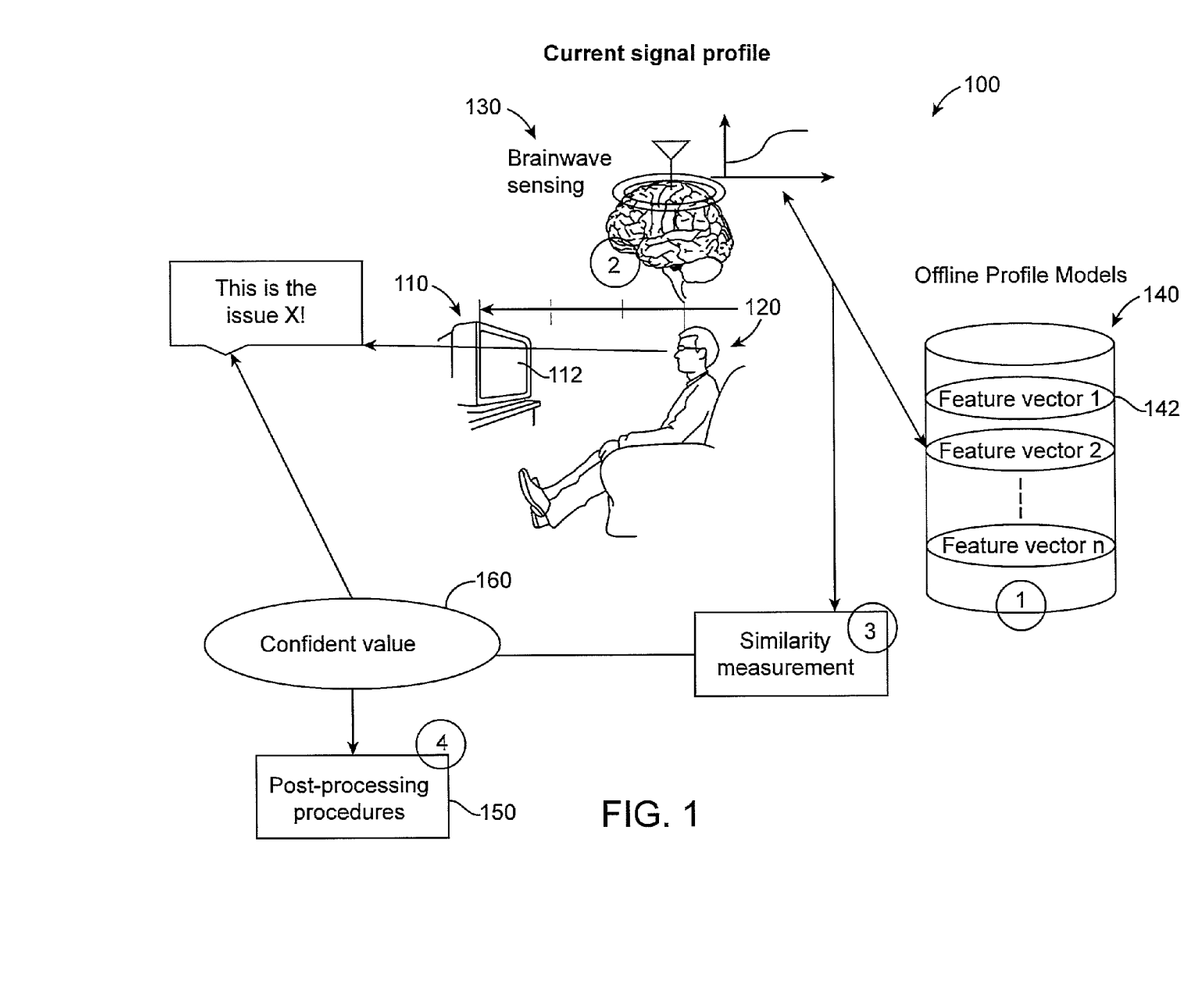
FIG. 1 is an illustration of a system for on-line decision making support in accordance with an embodiment.

FIG. 1 is an illustration a system 100 for on-line decision making support in accordance with an exemplary embodiment, which detects brainwave activity. As shown in FIG. 1, the system for on-line decision making support 100 can includes an optional visual display 110, a subject 120, a brainwave sensing device 130, and a computer device or data processing system 140.

The visual display 110 can be any suitable monitor or screen like device, which displays an image via an image screen 112. Alternatively, the visual display 110 can be a medical device such as an endoscope, which includes a camera or the like, and produces an image, which the subject 120 views via a visual screen 112 within the device.

In accordance with an aspect, the subject 120 performs an on-line or real-time task or activity, which includes the visual inspection or observation of a visual display or image screen 110. For example, video surveillance system operators and visual inspectors for product lines view one or more display monitors or screens or objects, which appear rapidly in order to identify operational threats or suspected issues. In accordance with another aspect, the task or activity can be one that the subject performs without a visual display. For example, a visual inspector on a production line.

The brainwave sensing device 130 is a device, which records electrical activity along the scalp. For example, the brainwave sensing device 130 can be an electroencephalography (EEG), which measures voltage fluctuations resulting from ionic current flows within the neurons of the brain. An EEG can obtain recordings of the brain's spontaneous electrical activity over a short period of time, for example 20 to 40 minutes, as recorded from multiple electrodes placed on the scalp. An EEG is generally described in terms of rhythmic activity and transients. The rhythmic activity is divided into bands by frequency. The frequency bands are usually extracted using spectral methods. However, any type of device, which senses electrical activity along the scalp, can be used.

For example, an EEG uses a plurality of electrodes, which detect the voltage fluctuations. The plurality of electrodes can be in the form of a cap or netting, which places the plurality of electrodes in one or more desired location along the scalp. Alternatively, the electrode can be positioned on the subject individually or by any suitable manner. In addition, touchless sensors or other sensors, which do not make contact with the scalp of the subject, can be used to detect the electrical activity.

The electrical activity from the brainwave sensing device 130 is transmitted via a connection or wire to the data processing system. The sensing device 130 can alternatively include wireless technology, which transmits the data or electrical activity obtained from the subject 120 to the data processing system 140 without a hard connection or wire.

In accordance with an embodiment, the data processing system or computer device 140 has executable instructions for generating a confident value 142 for recorded electrical activity from the brainwave device 130. The brainwave sensing device 130 senses brainwave signals of a subject 120 upon detection of a decision making process during a performance of an activity or task. The electrical activity of the subject is recorded over one or more frequency bands, and upon completing the decision making process, the recorded electrical activity is released to a data processing system 140 for analysis. The recorded electrical activity is compared with a profile model 142 for the subject, and a confident value 160 is calculated for the recorded electrical activity against the profile model 142 for the subject 120. If the confident value 160 does not meet a predefined threshold, a post-processing procedure 150 can be performed, wherein the predefined threshold represents a desired performance of the subject on the activity or task.

For an EEG, the frequency bands recorded can be between approximately 0 hertz ("Hz") to approximately 100 hertz (Hz) or greater, for example, 4 Hz to 30 Hz. Each of the frequency bands can be generally classified within one or more frequency bands. For example, frequencies of 4 hertz or lower can be assigned to the delta band, theta (θ) from approximately 5 to 7 Hz, alpha (α) from approximately 8 to 15 Hz, beta (β) approximately 16 to 24 Hz, and gamma (γ)

approximately 24 to 40 Hz. For example, the delta wave is a high amplitude brain wave with a frequency of oscillation between 0 to 4 hertz. Delta waves, like other brain waves, are recorded with an electroencephalogram (EEG) and are usually associated with the deepest stages of sleep (3 and 4 NREM), also known as slow-wave sleep (SWS), and aid in characterizing the depth of sleep. Thus, for an on-line decision making support system, the frequency bands will generally be 4 Hz or greater. In addition, the bands of frequencies as identified above are examples, and the one or more frequency bands can be defined by different frequencies. For example, for an EEG, the one or more frequency bands can be defined as delta ($\Delta$), less than 4 hertz, theta ($\theta$) approximately 4 to 8 Hz, alpha ($\alpha$) approximately 8 to 13 Hz, beta ($\beta$) approximately 13-30 Hz, and gamma ($\gamma$) approximately 30 to 100 Hz.

For example, by using one or more frequency bands with an EEG, the EEG alpha ($\alpha$) signal changes between correct and incorrect responses can suggest a measure of efficient use in attention processes. Furthermore, theta ($\theta$) and alpha ($\alpha$) signal synchronization can also help to differentiate between hits, false alarms and correct rejections. In addition, a distinct cognitive processing pattern by the synchronization of EEG theta and alpha powers is known to be apparent in approximately 90% of the subjects beginning with the presentation of the image and ending with the threat and/or non-threat decision.

According to an embodiment, a method for on-line judgment support is disclosed, which includes obtaining an offline or training EEG profile modeling (or profile model) during a skill acquisition or task, obtaining a real-time EEG sensing module, calculating an EEG based confident measurement, and performing a post-processing procedure, if needed. Based on the above method, a system for decision making support can be provided by measuring the similarity of the current EEG signals with each profile model associated to each decision result. For example, the closer or more similar, the EEG signal matches one of the profile models, the more reliable the results. Alternatively, once a less reliable result is detected, a post-process procedure can be conducted so as to reduce false judgments and improve the total productivity of the subject for the same or similar skills and tasks.

In measuring the similarity of the current EEG signal with one or more profile models, the detection or start of the decision making process can be obtained using a locking method, which can be used to set up the analysis window of electrical activity or Event-Related Potential (EPR) signals for each activity or task. The locking method detects an event-related brain potential, or increase in electrical activity as the surface of the brain, which is thought to reflect the preparation of motor activity on a certain side of the body. Accordingly, the detection of the increased electrical activity can be used to begin the recordation of electrical signals for a subject performing an activity or task.

For example, the locking methods can include stimulus-locked, response-locked, eye-tracking-locked and/or fixation-locked (FLEPR). The stimulus-locked method is measured with respect to the moment the eliciting stimulus appeared. The response-locked method is measured with respect to the moment the subject performed the actual motor activity (as measured by the execution of the movement or by recording muscle activity in the effector). Alternatively, the detection of the start of the decision making process can be eye-tracking or fixation locked, which is the process of measuring either the point of gaze ("where we are looking") or the motion of an eye relative to the head. An eye tracker is a device for measuring eye positions and eye movement. For example, a number of methods for measuring eye movement are available, which include using video images from which the eye position is extracted.

In accordance with an aspect, the analysis window of detected electrical signals can vary from the initial detection of a decision making process to a completion of the activity or task. Alternatively, the analysis window of detected electrical signals can include the detection for each and every detected decision making process over the entirety of the performance of the task, wherein the window includes a plurality of windows of detected electrical signals. In addition, the recorded activity can include one set of data, which is released to the data processing system upon completion of the activity or task, or alternatively, the recorded activity can be released upon completion of each of the plurality of decision making processes detected within the entirety of the activity or task. If the recorded activity is released upon completion of each and every one of the plurality of decision making processes and one or more confident values are calculated, the system and method can be used to alert one of a performance of the subject, which is below a desired performance level before completion of the activity or task. Thus, by alerting one of a subject's performance before completion of the activity or task, potential reductions in productivity, and/or injury to the subject or others may be avoided.

Figure 2:
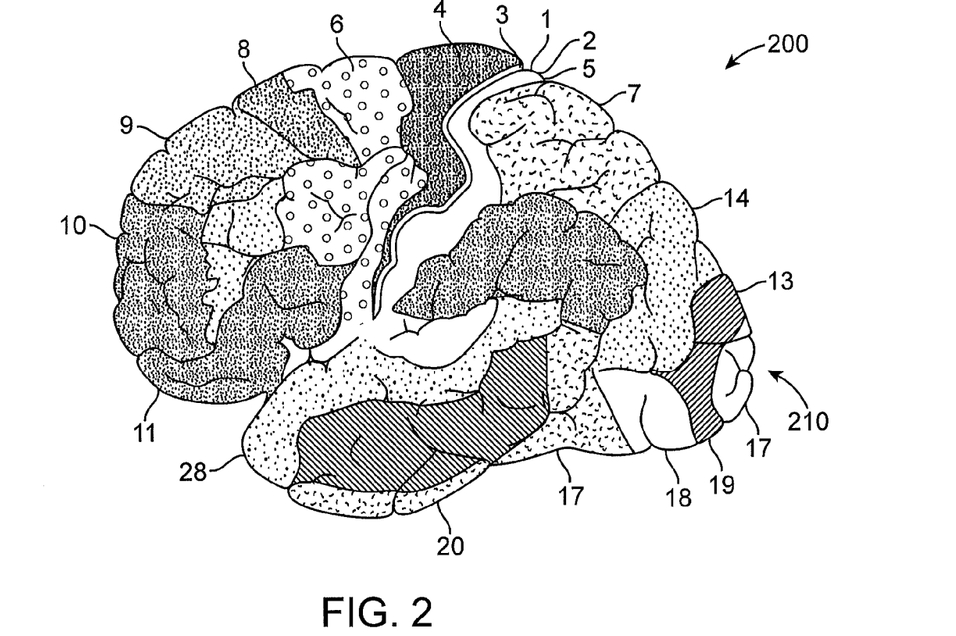
FIG. 2 is an illustration of a human brain and the identification of one or more locations for placement of electrodes of an electroencephalography (EEG) in accordance with an embodiment.

FIG. 2 is an illustration of a human brain 200 and the identification of one or more locations for placement of electrodes of an electroencephalography (EEG) in accordance with an embodiment. The electrodes of the brainwave sensing device 130 (or EEG) can be placed on the location of scalp, where visual stimuli (or signals) are actively analyzed and recognized, such as the left and right visual cortex or optical chiasm. The visual cortex of the brain is the part of the cerebral cortex responsible for processing visual information, and is located in the occipital lobe 210, in the back of the brain 200. The term visual cortex refers to the primary visual cortex (also known as striate cortex or V1) and extrastriate visual cortical areas such as V2, V3, V4, and V5. The primary visual cortex is anatomically equivalent to Brodmann area 17, or BA17. The extrastriate cortical areas consist of Brodmann area 18 and Brodmann area 19. A visual cortex is located in each hemisphere of the brain. The left hemisphere visual cortex receives signals from the right visual field and the right visual cortex from the left visual field.

Figure 3:
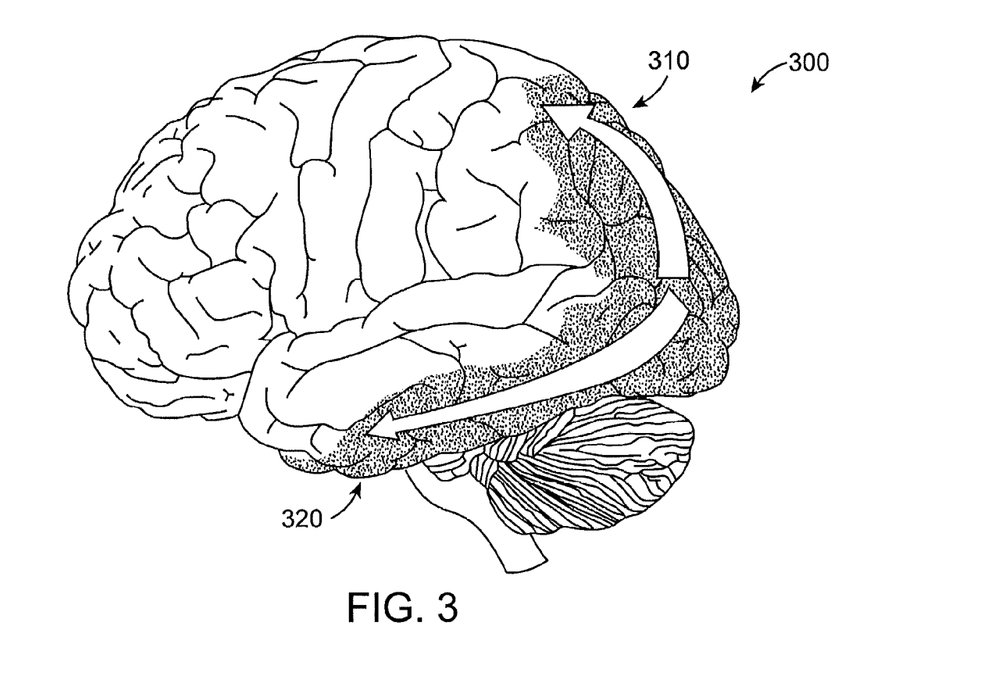
FIG. 3 is an illustration of a human brain and the identification of one or more locations for placement of electrodes of an EEG in accordance with an embodiment.

FIG. 3 is an illustration of a human brain 300 and the identification of one or more locations for placement of electrodes of an EEG in accordance with an embodiment. The dorsal stream 310 begins with V1, goes through Visual area V2, then to the dorsomedial area and Visual area MT (also known as V5) and to the posterior parietal cortex. The dorsal stream, sometimes called the "Where Pathway" or "How Pathway", is associated with motion, representation of object locations, and control of the eyes and arms, especially when visual information is used to guide saccades or reaching. The ventral stream 320 begins with V1, goes through visual area V2, then through visual area V4, and to the inferior temporal cortex. The ventral stream 320, sometimes called the "What Pathway", is associated with form recognition and object representation. It is also associated with storage of long-term memory. For example, in the agreed 10-20 International Placement System of EEG, they can be from $P_{[3,4]}$, $O_{[3,4]}$, or $F_{[3,4]}$. (See U. Herwig, P. Satrapi, C. Schönfeldt-Lecuona, "Using the International 10-20 EEG System for Positioning of Transcranial Magnetic Stimulation", Brain Topography, 24, vol. 16, no. 2, pp. 95-99, 2003).

In accordance with an embodiment, the sensing method can include the placement of one or more electrodes on the scalp of the subject using an electrode cap or netting. Alternatively, the electrodes can be individually placing the scalp of the subject as desired. In accordance with one aspect, the electrodes of EEG device are placed on the location of scalp, where visual stimuli (or signals) are actively analyzed and recognized, such as the left and right visual cortex or optical chiasm.

In accordance with an example, the signal extraction for the EEG is the raw voltage fluctuation (μV) signal between approximately 0 and 40 Hz within a defined or set period of time (for example, approximately 1 second just before the result released), which is collected by the EEG device. The raw signals are transferred into the frequency domain by FFT (Fast Fourier Transform) and divided into one or more frequency bands. For example, the one or more frequency bands can be defined as delta ($\Delta$), four or less Hz, theta ($\theta$) approximately 5 to 7 Hz, alpha ($\alpha$) approximately 8 to 15 Hz, beta ($\beta$) approximately 16 to 24 Hz, and gamma ($\gamma$) approximately 24-40 Hz. In accordance with another aspect, the one or more frequency bands can be defined delta ($\Delta$), less than 4 hertz ("Hz'), theta ($\theta$) approximately 4 to 8 Hz, alpha ($\alpha$) approximately 8 to 13 Hz, beta ($\beta$) approximately 13-30 Hz, and gamma ($\gamma$) approximately 30 to 100 Hz. The spectrum can also be obtained as the power of each of the one or more frequency bands.

In accordance with an aspect, each profile when the subject correctly identifies the visual target or non-target, is recorded and modeled as one or more feature vectors. For example, one feature vector could be $V=<\theta_l, \alpha_l, \beta_l, \gamma_l, \theta_r, \alpha_r, \beta_r, \gamma_r, \theta_d, \alpha_d, \beta_d, \gamma_d>$, which consists of the spectra from the left visual cortex, the right visual cortex, and the difference between the right visual cortex to the left visual cortex. Thus, a single spatiotemporal EEG response can be captured.

During the training or knowledge acquisition, one or more EEG profile models ($M_i$) are generated for each subject during an activity or task, wherein the subject is shown pictures or objects with a plurality of different target problems. For example, the plurality of different target problems can include products having manufacturing defects or flaw, or cancers in a radiology scan. In addition, depending on the complexity of visual inspection, each of the set of models can include a single target (or model) feature vector ($V_m$), or a plurality of feature vectors, wherein each of the plurality of feature vectors ($V_m$) is associated with a single problem.

During the performance of the activity or task, the brainwave signal (and electrical activity) of the subject is recorded for the same time period during which the EEG signal for the subject was collected during the profile acquisition or profile modeling. For example, one second just before the result issued, and wherein the electrical activity and features are extracted and processed as the current feature vector ($V_c$).

Based on the profile models (or EEG profile models) of the subject obtained during the training, the similarity between the current feature vector and one of the vectors among the set of profile models is calculated. For example, a similarity technique, such as Cosine Similarity or Euclidean Distance can be used. For example, Cosine $(V_c, V_m)=(V_c \cdot V_m)/(\|V_c\|\|V_m\|)$ or Euclidean Distance $(V_c, V_m)=$Sqrt (Sum of Squared Differences of two vectors).

Accordingly, by comparing the similarity value with a pre-defined threshold, the spatiotemporal EEG response, which is triggered when a target image is shown among a sequence of non-target and/or distractor images produces a result, which can be used for on-line decision making support.

In accordance with an aspect, upon the generation of a need for a post processing procedures, the post processing procedures 150 can include requesting the subject to repeat the task; repeating the task with another subject and if the profile model or result is the same, accepting the profile model or result as a higher confident value; alerting the profile model for the subject of the recorded activity with a special mark for future usage; and if the profile model and recorded electrical activity detects a new case, generating a new profile model for the subject and entering the profile into the set of profile models for the subject.

Figure 4:
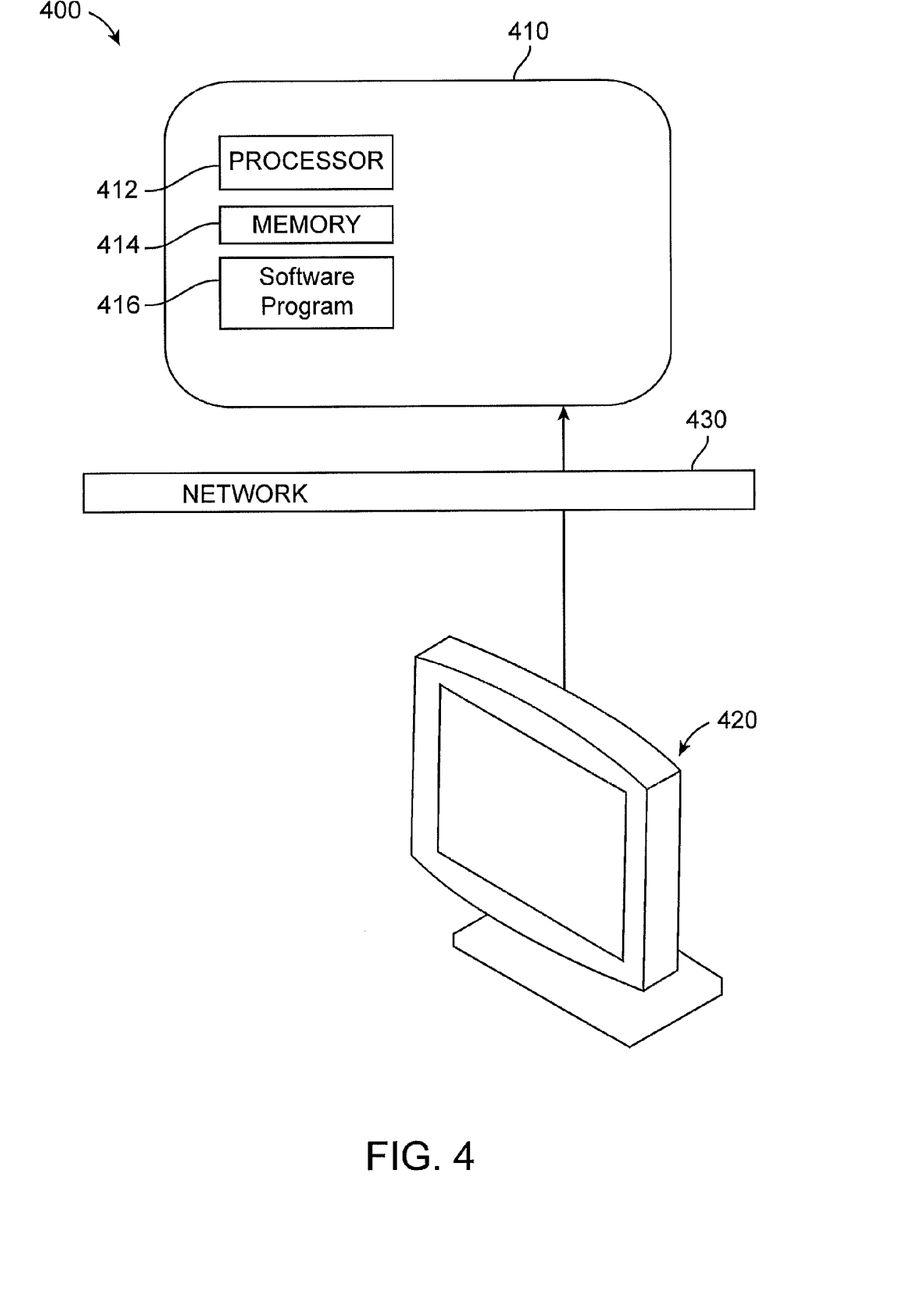
FIG. 4 is an illustration of a data processing system, which includes a client device or general purpose computer for a system and method of on-line decision making support.

FIG. 4 is an illustration of a system 400 for processing a method and system of on-line decision making support. As shown in FIG. 4, the system 400 includes a computer device or data processing system 410 for calculating the confident value for the recorded electrical activity against the profile model as disclosed herein. The data processing system 410 includes a processor or central processing unit (CPU) 412, one or more memories 414 for storing software programs 416 and data (such as files to be printed). The data processing system 410 also includes an operating system (OS), which manages the computer hardware and provides common services for efficient execution of various software programs 416. The processor or CPU 412 carries out the instructions of a computer program, which operates and/or controls at least a portion of the functionality of the data processing system 410. Examples of data processing system 410 include and are not limited to personal computers and/or personal digital assistants (PDAs).

The operating system acts as an intermediary between the software programs and hardware components within the data processing system 410. The operating system (or OS) manages the computer hardware and provides common services for efficient execution of application software.

The data processing system 410 can be connected to a video display monitor 420 via a network 430 for displaying the results of the comparison of the recorded electrical activity against the profile model for the subject in the form of the confident value. The video display monitor 420 can be a device having a screen, which display an image including but not limited to computers, monitors, and/or personal digital assistants (PDAs). Examples of the network 430 consistent with embodiments of the invention include, but are not limited to, the Internet, an intranet, a local area network (LAN) and a wide area network (WAN). The client device 410 and the video display monitor 420 can also be connected with a wire and/or wireless technology by using radio frequency (RF) and/or infrared (IR) transmission.

Figure 5:
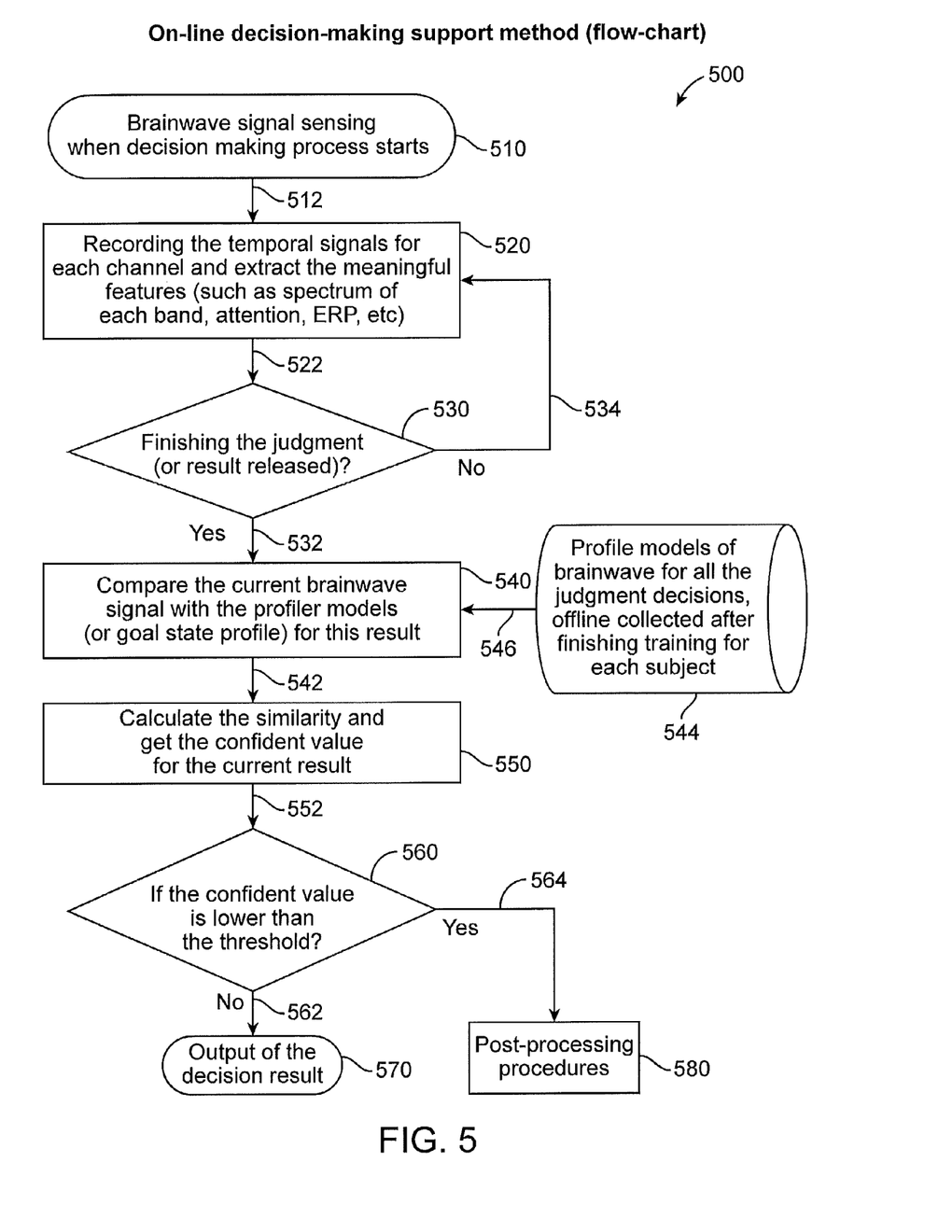
FIG. 5 is an illustration a flow chart for an on-line decision making support system in accordance with an embodiment.

FIG. 5 is an illustration a flow chart for an on-line decision making support system 500 in accordance with an embodiment. As shown in FIG. 5, the on-line decision-making support system 500 includes in step 510, sensing brainwave signals of a subject when a decision making process starts. If the decision making process is detect in step 512, the temporal signals for each channel is recorded and the meaningful features of the temporal signals are extracted in step 520. For example, the meaningful features can include spectrum of each band, attention, and/or electron paramagnetic resonance (ERP).

In step 530, if the decision making process has finished, e.g., the judgment and/or decision making process has been completed by the subject, in step 532, the results are released to a data processing system. If the judgment and/or decision making process has not yet been completed, in step 534, the process continues to record the temporal signals for each channel until the decision making process has been completed.

In step 540, the current brainwave signals (e.g., recorded temporal signals) are compared with one or more profiler models or goal state profiles for the subject to determine a confident value. The one or more profiler models or goal state profiles can be established models or profiles for the subject. Alternatively, the models or profiles can be established based on one or more previous test and analysis of the task and/or a similar task, which provides a profile model, if the profile model for the activity or task for the subject has not been previously established. The obtained results and the profiler models are forward for comparison via step 542 to generate a confident value 552 in step 550.

For example, in step 544, profile models of brainwave signals and electrical activity for one or more judgment decisions are collected offline after finishing training for each subject. The profile models in step 546 are provided to the data processing system, which compares the current brainwave signals and electrical activity of the subject with the profiler models (of goal state pattern profile) for the obtained results.

In step 550, the obtained results and the profiler model after comparison are used to calculate the similarity of the obtained results and the profiler model to generate a confident value 552 for the current results.

Once the confident value 552 has been generated, if the confident value 552 is greater than a predetermined or predefined threshold 560, in step 562, the results of the decision are output 570 for review, which indicates that the subject performed as expected or within a reasonable tolerance level for the task. Alternatively, if the confident value is less than the predetermined or predefined threshold 560, in step 564, the results are used to conduct a post-processing procedure 580.

The post-processing procedure 580 can include requesting the subject to repeat the task; repeating the task with another subject and if the profile model or result is the same, accepting the profile model or result as a higher confident value; alerting the profile model for the subject of the recorded activity with a special mark for future usage; and if the profile model and recorded electrical activity detects a new case, generating a goal state pattern profile (or new profile model) for the subject and entering the goal state pattern profile with the profile models for the subject.

Figure 6:
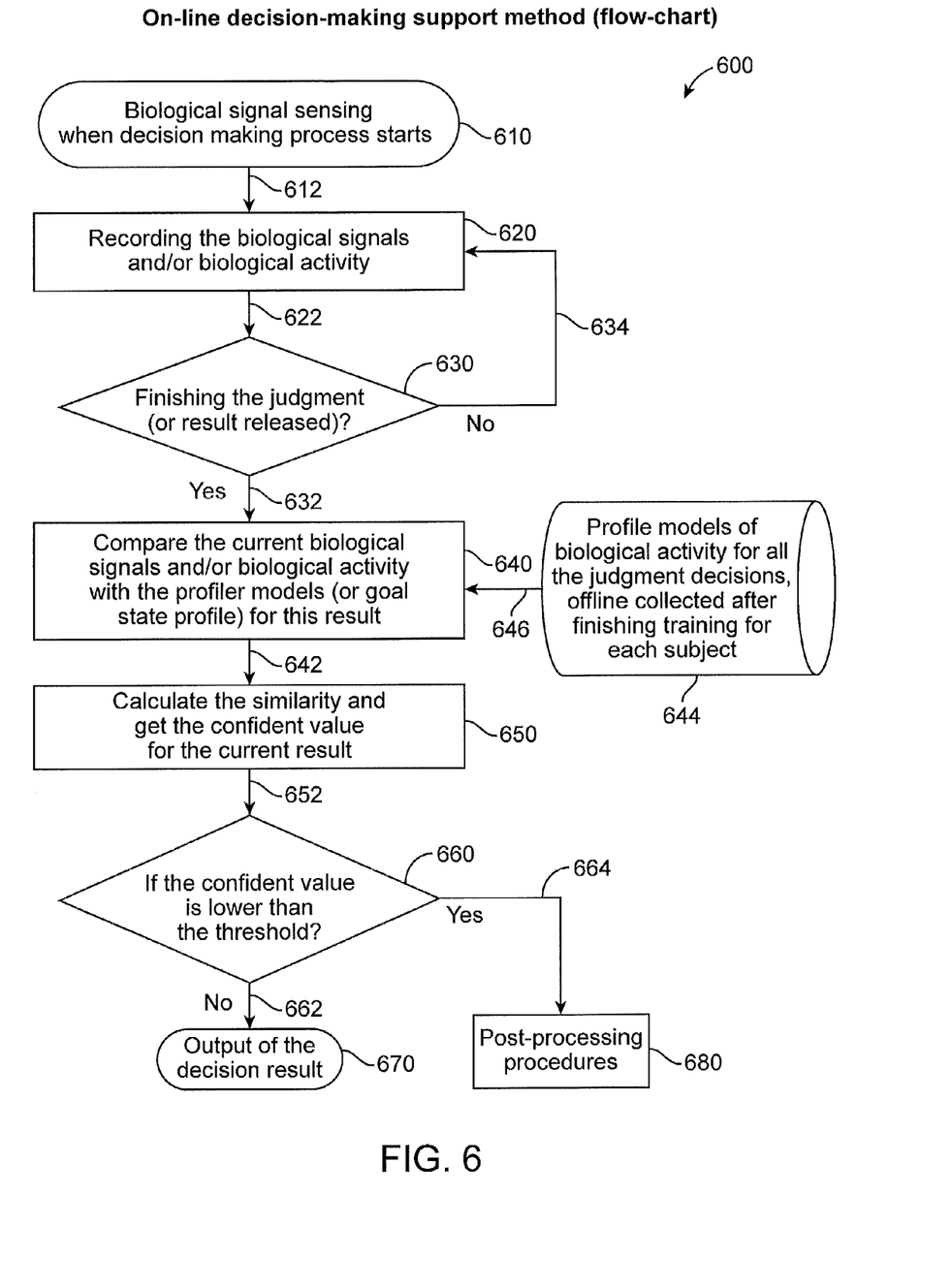
FIG. 6 is an illustration of a flow chart for an on-line decision making support system in accordance with another exemplary embodiment.

FIG. 6 is an illustration a flow chart for an on-line decision making support system 600 in accordance with another exemplary embodiment, which includes any biological activity. As disclosed herein, the biological activity relates to the study of life and living organisms, which can include biological activities such as perspiration or sweat, heart rate, nervous signals, brain waves, and/or combinations thereof. As shown in FIG. 6, the on-line decision-making support system 600 includes in step 610, sensing biological signals of a subject when a decision making process starts. If the decision making process is detect in step 612, the biological signals and/or biological activity is recorded and the meaningful features of the biological signals and/or biological activity are extracted in step 620.

In step 630, if the decision making process has finished, e.g., the judgment and/or decision making process has been completed by the subject, in step 632, the results are released to a data processing system. If the judgment and/or decision making process has not yet been completed, in step 634, the process continues to record the biological signals and/or biological activity until the decision making process has been completed.

In step 640, the current biological signals and/or biological activity are compared with one or more profiler models or goal state profiles for the subject to determine a confident value. The one or more profiler models or goal state profiles can be established models or profiles for the subject. Alternatively, the models or profiles can be established based on one or more previous test and analysis of the task and/or a similar task, which provides a profile model, if the profile model for the activity or task for the subject has not been previously established. The obtained results and the profiler models are forward for comparison via step 642 to generate a confident value 652 in step 650.

For example, in step 644, profile models of biological signals and/or biological activity for one or more judgment decisions are collected offline after finishing training for each subject. The profile models in step 646 are provided to the data processing system, which compares the current biological signals and/or biological activity of the subject with the profiler models (of goal state pattern profile) for the obtained results.

In step 650, the obtained results and the profiler model after comparison are used to calculate the similarity of the obtained results and the profiler model to generate a confident value 652 for the current results.

Once the confident value 652 has been generated, if the confident value 652 is greater than a predetermined or predefined threshold 660, in step 662, the results of the decision are output 670 for review, which indicates that the subject performed as expected or within a reasonable tolerance level for the task. Alternatively, if the confident value is less than the predetermined or predefined threshold 660, in step 664, the results are used to conduct a post-processing procedure 680.

The post-processing procedure 680 can include requesting the subject to repeat the task; repeating the task with another subject and if the profile model or result is the same, accepting the profile model or result as a higher confident value; alerting the profile model for the subject of the recorded activity with a special mark for future usage; and if the profile model and recorded electrical activity detects a new case, generating a goal state pattern profile (or new profile model) for the subject and entering the goal state pattern profile with the profile models for the subject.

In accordance with another exemplary embodiment, a non-transitory computer readable medium containing a computer program for on-line decision making support, comprising: sensing brainwave signals of a subject upon detection of a decision making process during a performance of a task; recording electrical activity of the subject over one or more frequency bands; completing the decision making process and releasing the recorded electrical activity to a data processing system for analysis; comparing the recorded electrical activity with a profile model for the subject; calculating a confident value for the recorded electrical activity against the profile model for the subject, and performing a post-processing procedure if the confident value does not meet a predefined threshold, wherein the predefined threshold represents a desired performance of the subject on the task.

In accordance with an exemplary embodiment, a non-transitory computer readable medium containing a computer program for on-line decision making support, comprising: sensing biological signals of a subject upon detection of a decision making process during a performance of a task; recording biological activity of the subject; completing the decision making process and releasing the recorded biological activity to a data processing system for analysis; comparing the recorded biological activity with a profile model for the subject; calculating a confident value for the recorded biological activity against the profile model for the subject, and performing a post-processing procedure if the confident value does not meet a predefined threshold, wherein the predefined threshold represents a desired performance of the subject on the task.

The non-transitory computer usable medium may be a magnetic recording medium, a magneto-optic recording medium, or any other recording medium which will be developed in future, all of which can be considered applicable to the present invention in all the same way. Duplicates of such medium including primary and secondary duplicate products and others are considered equivalent to the above medium without doubt. Furthermore, even if an embodiment of the present invention is a combination of software and hardware, it does not deviate from the concept of the invention at all. The present invention may be implemented such that its software part has been written onto a recording medium in advance and will be read as required in operation.

The method and system for on-line decision making support as disclosed herein may be implemented using hardware, software or a combination thereof. In addition the method and system for on-line decision making support as disclosed herein may be implemented in one or more computer systems or other processing systems, or partially performed in processing systems such as personal digit assistants (PDAs). In yet another embodiment, the invention is implemented using a combination of both hardware and software.

It will be apparent to those skilled in the art that various modifications and variation can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for on-line decision making support, comprising:
    sensing biological signals of a subject upon detection of a decision making process during a performance of a task, wherein the biological signals are brainwave signals;
    recording from the subject for a right hemisphere visual cortex and a left hemisphere visual cortex biological activity of the subject, wherein the biological activity is electrical activity recorded over one more frequency bands;
    completing the decision making process and releasing the recorded biological activity to a data processing system for analysis;
    generating a current feature vector consisting of spectra from the right visual cortex, the left visual cortex and a difference between the right visual cortex to the left visual cortex over the one or more frequency bands;
    comparing the current feature vector to a target feature vector from a profile model for the subject;
    calculating a confident value for the recorded biological activity against the profile model for the subject, and
    performing a post-processing procedure if the confident value does not meet a predefined threshold, wherein the predefined threshold represents a desired performance of the subject on the task.

2. The method of claim 1, wherein the step of calculating the confident value comprises:
    extracting one or more features from the recorded biological activity;
    generating one or more current feature vectors; and
    comparing the one or more current feature vectors to one or more target feature vectors among the profile model for the subject using at least one similarity technique.

3. The method of claim 2, wherein the at least one similarity technique is Cosine Similarity or Euclidean Distance.

4. The method of claim 1, wherein the one or more frequency bands include electrical signals between approximately 5 and 40 Hz, and the current and target feature vectors are generated using two or more frequency bands from the one or more frequency bands between approximately 5 and 40 Hz.

5. The method of claim 1, wherein the current and target feature vectors are spatiotemporal vectors.

6. The method of claim 1, comprising:
    generating at least one profile model for the subject after showing the subject one or more tasks having different target problems.

7. The method of claim 6, wherein the at least one profile model for each subject comprises a plurality of profile models, each of the plurality of profile models having at least one target feature vector.

8. The method of claim 7, comprising:
    calculating a similarity between the current feature vector generated from the recorded electrical activity and a target vector among the at least one target feature vectors from the profile model of the subject to calculate the confident value.

9. The method of claim 1, wherein the detection of the decision making process comprises a locking mechanism, the locking mechanism including one or more of the following locking mechanisms:
    a stimulus-locked, a response-locked, an eye-tracking-locked, and/or a fixation-locked (FLEPR) method.

10. The method of claim 1, wherein the post-processing procedure includes one or more of the following:
    requesting the subject to repeat the task; and/or
    marking the profile model for the subject with a special mark for future usage.

11. A system for on-line decision making, comprising:
    a biological sensing device; and
    a computer device having executable instructions for generating a confident value for recorded biological activity from the biological sensing device, the instructions causing the computer device to perform the steps of:
    sensing biological signals of a subject upon detection of a decision making process during a performance of a task, wherein the biological signals are brainwave signals;
    recording from the subject for a right hemisphere visual cortex and a left hemisphere visual cortex biological activity of the subject, wherein the biological activity is electrical activity recorded over one or more frequency bands;
    completing the decision making process and releasing the recorded biological activity to a data processing system for analysis;
    generating a current feature vector consisting of spectra from the right visual cortex, the left visual cortex and a difference between the right visual cortex to the left visual cortex over the one or more frequency bands;
    comparing the current feature vector to a target feature vector from a profile model for the subject;
    calculating a confident value for the recorded biological activity against the profile model for the subject, and
    performing a post-processing procedure if the confident value does not meet a predefined threshold, wherein the predefined threshold represents a desired performance of the subject on the task.

12. The system of claim 11, wherein the step of calculating the confident value comprises:

extracting one or more features from the recorded biological activity;
generating one or more current feature vectors; and
comparing the one or more current feature vectors to one or more target feature vectors among the profile model for the subject using at least one similarity technique.

13. The system of claim 11, comprising:
a display for displaying visual features to a subject during the performance of the task.

14. The system of claim 11,
wherein the one or more frequency bands include electrical signals between approximately 5 and 40 Hz, and the current feature vector is generated using two or more frequency bands from the one or more frequency bands between approximately 5 and 40 Hz.

15. The system of claim 14, wherein the computer device:
generates at least one profile model for the subject after showing the subject one or more tasks having different target problems, wherein the at least one profile model for the subject comprises a plurality of profile models, each of the plurality of profile models having at least one target feature vector; and
calculates a similarity between the current feature vector generated from the recorded electrical activity and a target vector among the at least one target feature vectors from the profile model of the subject to calculate the confident value.

16. The system of claim 11, wherein the post-processing procedure includes one or more of the following:
requesting the subject to repeat the task; and/or
marking the profile model for the subject with a special mark for future usage.

17. The system of claim 11, wherein the biological sensing device senses the brainwave activity using an electroencephalogram (EEG), wherein the EEG includes one or more electrodes, which detect visual stimuli or signals.

18. A non-transitory computer readable medium containing a computer program for on-line decision making support, the computer program having executable instructions, which, when executed, cause a computer device to perform the steps of:
sensing biological signals of a subject upon detection of a decision making process during a performance of a task, wherein the biological signals are brainwave signals;
recording from the subject for a right hemisphere visual cortex and a left hemisphere visual cortex biological activity of the subject, wherein the biological activity of the subject is electrical activity recorded over one or more frequency bands;
completing the decision making process and releasing the recorded biological activity to a data processing system for analysis;
generating a current feature vector consisting of spectra from the right visual cortex, the left visual cortex and a difference between the right visual cortex to the left visual cortex over the one or more frequency bands;
comparing the current feature vector to a target feature vector from a profile model for the subject;
calculating a confident value for the recorded biological activity against the profile model for the subject, and
performing a post-processing procedure if the confident value does not meet a predefined threshold, wherein the predefined threshold represents a desired performance of the subject on the task.

19. The computer readable medium of claim 18, wherein the step of calculating the confident value comprises:
extracting one or more features from the recorded biological activity;
generating one or more current feature vectors; and
comparing the one or more current feature vectors to one or more target feature vectors among the profile model for the subject using at least one similarity technique.

* * * * *